US012742038B2

(12) United States Patent
Bai et al.

(10) Patent No.: US 12,742,038 B2
(45) Date of Patent: Sep. 22, 2026

(54) PIEZOELECTRIC POLYLACTIC ACID MATERIAL AND PREPARATION METHOD AND APPLICATION THEREOF

(71) Applicant: NINGBO MICHI TECHNOLOGY CO., LTD., Ningbo (CN)

(72) Inventors: Hongwei Bai, Beijing (CN); Shihao Deng, Beijing (CN); Qiang Fu, Beijing (CN); Zeshuang Qiao, Beijing (CN); Qin Zhang, Beijing (CN); Ke Wang, Beijing (CN)

(73) Assignee: NINGBO MICHI TECHNOLOGY CO., LTD., Ningbo (CN)

(*) Notice: Subject to any disclaimer, the term of this patent is extended or adjusted under 35 U.S.C. 154(b) by 609 days.

(21) Appl. No.: 18/254,432

(22) PCT Filed: Oct. 10, 2022

(86) PCT No.: PCT/CN2022/124439

§ 371 (c)(1),
(2) Date: May 25, 2023

(87) PCT Pub. No.: WO2023/078033

PCT Pub. Date: May 11, 2023

(65) Prior Publication Data

US 2024/0002587 A1 Jan. 4, 2024

(30) Foreign Application Priority Data

Nov. 4, 2021 (CN) ........................ 202111299274.1

(51) Int. Cl.
*C08G 63/68* (2006.01)
*A61K 8/85* (2006.01)
(Continued)

(52) U.S. Cl.
CPC ................ *C08G 63/08* (2013.01); *A61K 8/85* (2013.01); *A61Q 11/00* (2013.01); *C08G 63/90* (2013.01);
(Continued)

(58) Field of Classification Search
None
See application file for complete search history.

(56) References Cited

U.S. PATENT DOCUMENTS 5,792,508 A * 8/1998 Kitamura ................ A61K 8/65 424/49
2017/0179370 A1 6/2017 Kim et al.
2021/0052358 A1* 2/2021 Wang .................. A61C 19/066

FOREIGN PATENT DOCUMENTS

AU 2010224400 A1 * 10/2010
CN 106947228 A 7/2017
(Continued)

OTHER PUBLICATIONS

Long, Lin; "Preparation and Properties of Poly (Lactic Acid) Porous Gel"; Qingdao University of Science & Technology Professional Master Decgree Thesis; Jan. 15, 2018; ISSN: 1674-0246; pp. 1-67.
(Continued)

*Primary Examiner* — Tae H Yoon
(74) *Attorney, Agent, or Firm* — NKL Law; Allen Xue

(57) ABSTRACT

A piezoelectric polylactic acid material has a layered stacking structure, and a porous structure is formed between stacked layers. The piezoelectric polylactic acid material has a piezoelectric constant of 5.2-35.3 pC/N, has the ability to efficiently catalyze dye/pigment degradation, and can be used in the fields of dye/pigment degradation and tooth whitening. A preparation method for the piezoelectric polylactic acid composite material is also provided.

13 Claims, 4 Drawing Sheets

(51) Int. Cl.
*A61Q 11/00* (2006.01)
*C08G 63/08* (2006.01)
*C08G 63/90* (2006.01)

(52) U.S. Cl.
CPC ...... *A61K 2800/54* (2013.01); *A61K 2800/92* (2013.01)

(56) References Cited

FOREIGN PATENT DOCUMENTS

| | | | | |
|---|---|---|---|---|
| CN | 107670108 | A | * | 2/2018 |
| CN | 110464674 | A | | 11/2019 |
| CN | 114058165 | A | | 2/2022 |
| EP | 0510999 | A1 | * | 10/1992 |
| JP | WO2006095023 | A1 | * | 8/2008 |
| JP | 2020130495 | A | * | 8/2020 |
| WO | WO 2011145391 | A1 | * | 11/2011 |

OTHER PUBLICATIONS

Yang, Bowen; "Preparation and Applications of Polylactide-Based Chiral Porous Materials"; China Academic Journal Electronic Publishing House; Jan. 15, 2019; ISSN: 1674-0246; pp. 1-86.

Sun, Xiao-Rong et al.; "A Green and Facile Melt Approach for Hierarchically Porous Polylactide Monoliths Based on Stereocomplex Crystllite Net work"; ACS Sustainable Chemistry & Engineering; vol. 5; Aug. 14, 2017; ISSN. 2168-0485; pp. 8334-8343.

Xie, Yan et al.; "High-performance porous polylactide stereocomplex crystallite scaffolds prepared by solution blending and salt leaching"; Materials Science & Engineering C; vol. 90; May 6, 2018; ISSN. 0928-4931; pp. 602-609.

Chuaponpat, Natthapong et al.; "Morphology, Thermal and Mechanical Properties of Co-Continuous Porous Structure of PLA/PVA Blends by Phase Separation"; Polymers; vol. 12, May 9, 2020; ISSN. 2073-4360; pp. 1-20.

* cited by examiner

PIEZOELECTRIC POLYLACTIC ACID MATERIAL AND PREPARATION METHOD AND APPLICATION THEREOF

FIELD OF TECHNOLOGY

The present disclosure belongs to the technical field of polylactic acid materials and preparation thereof, and specifically relates to a piezoelectric polylactic acid material and a preparation method and application thereof.

BACKGROUND

With continuous pursuit of colorful and diversified visual beauty in the human society, natural/synthetic dyes have been gradually applied in eating, wearing, living and walking of the human life. Accordingly, the human civilization is greatly enriched, and human living standards are also greatly improved. Meanwhile, on the one hand, a large number of dyes are discharged into nature through textiles, food and printing industrial wastewater, and these dyes with stable chemical structures can exist stably in the natural cycle for a long time, leading to sustained harm to the ecological environment. On the other hand, many problems caused by dyeing with dyes/pigments are also difficult to solve in daily life, such as fabric dyeing and tooth staining. A physical adsorption method (such as adsorption with activated carbon) is usually used in the industry for treating dye wastewater so as to meet discharge standards. By means of the dye treatment method, dyes are only transferred from a water dispersion medium to a solid medium, so that the harm of the dyes is not fundamentally removed, and secondary pollution is likely to be caused. However, in view of the problem of solid media (such as teeth) stained by dyes/pigments, a physical method (such as grinding and polishing) is less effective. The main reason is that as these solid media usually have very rich microstructures (such as tiny holes of the tooth enamel of teeth and twisted and woven structures of fabrics), favorable conditions are provided for attachment of the dyes. According to a basic principle of a chemical treatment method, a chemical reagent (such as a Fenton catalytic reagent, a high-concentration hydrogen peroxide ($H_2O_2$) solution and a sodium hypochlorite solution) with (or capable of producing) high oxidation is used for converting pigment molecules into colorless and harmless molecules through oxidation, degradation and other processes, so as to achieve the purposes of bleaching, decolorization and detoxification. The chemical treatment method usually has the disadvantages of high cost, one-time use, low efficiency, complex process and the like, and thus has been rarely used in treatment of industrial dye wastewater. Moreover, according to the chemical treatment method, most of highly efficient oxidation reagents are extremely toxic to the human body, and are not applicable to underwear bleaching, tooth whitening and other fields.

A piezoelectric material refers to a material having a voltage between two end surfaces when a certain external pressure is applied. By means of the voltage generated by the piezoelectric material under the condition of mechanical vibration, the formation of reactive oxidation species (ROS), such as hydroxyl radical (·OH), superoxide ion ($\cdot O^{2-}$) and singlet oxygen ($_1O^2$), in water can be effectively catalyzed. The ROS formed have strong oxidation ability, and can efficiently oxidize and degrade pigment molecules with stable chemical structures, such as crystal violet (CV), methylene blue (MB), indigo carmine (IC) and methyl orange (MO). Therefore, micron/nano piezoelectric materials prepared in small batches in laboratories have been continuously applied in degradation of dyes/pigments by researchers in recent years (Nat Commun, 2021, 12, 3508).

Common piezoelectric materials include piezoelectric ceramics (such as lead oxide and barium titanate ($BaTiO_4$)) and piezoelectric polymers (such as polyvinylidene fluoride (PVDF) and poly(L-lactic acid) (PLLA)). The piezoelectric materials can be divided into two categories according to piezoelectric principles. The I category of piezoelectric materials achieve piezoelectric properties through polarization in a high electric field. With PVDF as an example, the PVDF is usually polarized by applying a voltage in a high temperature molten state, and effects of an electric field are removed after the PVDF is completely cooled and shaped, so as to freeze the PVDF in a polarized state. However, due to relaxation characteristics of a polymer, this semi-permanent electret cannot maintain piezoelectric properties for a long time. The II category of piezoelectric polymers are composed of chiral molecular chains, and can be polarized by rotation of chiral centers through mechanical action without polarization treatment in an external electric field. For example, polylactic acid with a chiral repeating unit can show certain shear piezoelectric properties. Although the common I category of piezoelectric ceramics (such as $BaTiO_4$) and piezoelectric polymers (such as PVDF) have better piezoelectric properties, these materials can only achieve excellent piezoelectric properties after polarization treatment in an external electric field, and are not applicable to continuous treatment of industrial dye wastewater. Secondly, non-degradable or difficult-to-degrade piezoelectric polymers are converted into microplastics after entering the natural cycle, leading to secondary pollution of the ecological environment. In addition, the common piezoelectric materials have poor biocompatibility and usually have high biotoxicity, and are thus difficult to be used in applications related to the human body (such as piezoelectric promoted bone tissue repair and piezoelectric tooth whitening). At present, green, environmentally friendly and safe piezoelectric materials which can be used for efficient degradation of dyes/pigments are still blank in the market, and are required to be developed urgently.

Polylactic acid (PLA) is a bio-based fully biodegradable green polymer. The waste PLA can be completely degraded into non-toxic and harmless water ($H_2O$) and carbon dioxide ($CO_2$) in the natural cycle. The PLA has the advantages of being excellent in mechanical properties, good in biocompatibility, free of toxicity and mild, and has been widely used in the field of biomedical materials, including surgical sutures, bone repair materials, biological dressings, drug slow-release materials and the like. Meanwhile, the PLA shows shear piezoelectric properties due to a chiral center in a molecular chain, and can generate a voltage under mechanical vibration without polarization treatment. Although the piezoelectric properties of the PLA are slightly lower than that of traditional piezoelectric materials, the PLA can also show an extremely high piezoelectric signal after specific structural design and a processing and shaping method. For example, a stereoscopic composite type polylactic acid (SC-PLA) nanofiber nonwoven piezoelectric membrane with an open-circuit output voltage close to 4 V was prepared by Lv Jun et al. based on an orientation effect of electrostatic spinning on a PLA crystal (J. Mater. Chem. A, 2019, 7, 1810-1823). Therefore, the PLA is a green and safe piezoelectric material with great potential for development.

SUMMARY

In view of the problems of the prior art, the purpose of the present disclosure is to provide a piezoelectric polylactic acid composite material. The microstructure of the obtained composite material is a layered stacking structure, and a porous structure is formed between stacked layers. The polylactic acid with the structure has high piezoelectric properties, thereby having the ability to efficiently catalyze dye/pigment degradation. In addition, the present disclosure further provides a preparation method of the piezoelectric polylactic acid composite material. The method is simple and efficient, and industrial production is easy to realize.

The technical solutions adopted by the present disclosure are as follows.

The first technical problem to be solved by the present disclosure is to provide a piezoelectric polylactic acid material. The microstructure of the piezoelectric polylactic acid material is a layered stacking structure, and a porous structure is formed between stacked layers.

Further, the piezoelectric polylactic acid material has a piezoelectric constant ($d_{33}$) of 5.2-35.3 pC/N.

Further, the piezoelectric polylactic acid material is prepared by the following method: ×subjecting poly(L-lactic acid), poly(D-lactic acid) and a pore-forming agent to melting and blending at 170-220° C. to obtain a blend; and then removing the pore-forming agent to obtain the piezoelectric polylactic acid material, where the pore-forming agent has good compatibility with the polylactic acid. The pore-forming agent has good compatibility with the polylactic acid indicates that the blend obtained after the two substances are subjected to melting and blending has only one glass transition temperature; and that is to say, mixing at the molecular level can be realized after the two substances are subjected to melting and blending, phase separation does not occur in a molten state, and a homogeneous structure is obtained.

Further, the pore-forming agent is a polymer or a small molecule having good compatibility with the polylactic acid.

Preferably, the pore-forming agent is selected from any one of polyethylene glycol (PEG), polyvinyl acetate (PVAc), polymethyl methacrylate (PMMA), polyhydroxybutyric acid (PHB), tributyl citrate (TBC), or dioctyl phthalate (DOP).

Further, the ratio of the poly(L-lactic acid) to the poly(D-lactic acid) to the pore-forming agent is as follows: 30-70 parts by weight of the poly(L-lactic acid), 30-70 parts by weight of the poly(D-lactic acid) and 10-50 parts by weight of the pore-forming agent.

Further, in the preparation method of the piezoelectric polylactic acid material, the raw material further includes a compatibilizer, and the use amount of the compatibilizer is 0.1-0.6 part by weight, preferably 0.3-0.4 part by weight.

Further, the compatibilizer is an amphiphilic compound having good compatibility with both the polylactic acid and the pore-forming agent; and preferably, the compatibilizer is any one of a polyethylene oxide-propylene oxide-ethylene oxide (PEO-PPO-PEO) block copolymer, a polyethylene oxide-propylene oxide (PEO-PPO) block copolymer, a polyethylene oxide-lactic acid-ethylene oxide (PEO-PLA-PEO) block copolymer, and a polyethylene oxide-butyl acrylate (PEO-PBA) block copolymer.

Further, the poly(L-lactic acid) (PLLA) has a weight-average molecular weight of $1*10^4$-$5*10^6$ g/mol and an optical purity of equal to or greater than 90%; and the poly(D-lactic acid) (PDLA) has a weight-average molecular weight of $1*10^4$-$5*10^6$ g/mol and an optical purity of equal to or greater than 90%.

Further, in the above preparation method of the piezoelectric polylactic acid material, the pore-forming agent is removed by the following method: placing the blend in a solvent capable of dissolving the pore-forming agent but not capable of dissolving the polylactic acid, and conducting full etching to remove the pore-forming agent. After the pore-forming agent is removed by the method, a resulting product is required to be washed and dried.

Further, the solvent is selected from one of water, ethanol, acetone, cyclohexane, n-hexane, dichloromethane, or trichloromethane.

For example, when the pore-forming agent is PEG, the optional solvent may be water or ethanol, because the PEG is soluble in water or ethanol while the PLA is insoluble.

Further, in the above preparation method of the piezoelectric polylactic acid material, the poly(L-lactic acid), the poly(D-lactic acid) and the pore-forming agent are subjected to melting and blending at 170-220° C. for 3-10 min to obtain a blend.

Further, in the above preparation method of the piezoelectric polylactic acid material, the melting and the blending are conducted at a temperature of 200-220° C.

The second technical problem to be solved by the present disclosure is to provide a preparation method of the piezoelectric polylactic acid material. The preparation method includes: subjecting poly(L-lactic acid), poly(D-lactic acid) and a pore-forming agent to melting and blending at 170-220° C. to obtain a blend; and then removing the pore-forming agent to obtain the piezoelectric polylactic acid material, where the pore-forming agent has good compatibility with the polylactic acid. The pore-forming agent has good compatibility with the polylactic acid indicates that the blend obtained after the two substances are subjected to melting and blending has only one glass transition temperature; and that is to say, mixing at the molecular level can be realized after the two substances are subjected to melting and blending, phase separation does not occur in a molten state, and a homogeneous structure is obtained.

Further, in the above preparation method of the piezoelectric polylactic acid material, the pore-forming agent is removed by the following method: placing the blend in a solvent capable of dissolving the pore-forming agent but not capable of dissolving the polylactic acid, and conducting full etching to remove the pore-forming agent. After the pore-forming agent is removed by the method, a resulting product is required to be washed and dried.

Further, in the above preparation method of the piezoelectric polylactic acid material, the poly(L-lactic acid), the poly(D-lactic acid) and the pore-forming agent are subjected to melting and blending at 170-220° C. for 3-10 min to obtain a blend.

Further, in the above preparation method of the piezoelectric polylactic acid material, the melting and the blending are conducted at a temperature of 200-220° C.

The third technical problem to be solved by the present disclosure is to provide use of the piezoelectric polylactic acid material in tooth whitening, dye/pigment degradation, piezoelectric sensing, ultrasonic imaging, in vivo drivers, or implantable piezoelectric devices for induced regeneration of tissues.

The fourth technical problem to be solved by the present disclosure is to provide a tooth whitening material. The tooth whitening material is a piezoelectric polylactic acid material. The microstructure of the piezoelectric polylactic acid material is a layered stacking structure, and a porous structure is formed between stacked layers.

Further, the piezoelectric polylactic acid material has a piezoelectric constant ($d_{33}$) of 5.2-35.3 pC/N.

Further, the piezoelectric polylactic acid material is prepared by the following method: subjecting poly(L-lactic acid), poly(D-lactic acid) and a pore-forming agent to melting and blending at 170-220° C. to obtain a blend; and then removing the pore-forming agent to obtain the piezoelectric polylactic acid material, where the pore-forming agent has good compatibility with the polylactic acid.

The fifth technical problem to be solved by the present disclosure is to provide a tooth whitening product. The tooth whitening product is a tooth whitening agent or a tooth whitening instrument containing the piezoelectric polylactic acid whitening material.

Further, the tooth whitening agent is a piezoelectric polylactic acid material or a tooth whitening composition containing a piezoelectric polylactic acid material.

Further, the tooth whitening agent is in a form of a powder, a liquid, a gum, a gel, a paste, or a fiber.

Further, the tooth whitening composition containing a piezoelectric polylactic acid material is a toothpaste, a tooth powder, a gum, a chew gum, a gel, a tooth cleaning solution, a tooth scrub, a mouthwash, or a medical floss containing piezoelectric polylactic acid.

Further, the tooth whitening instrument is a tooth whitening instrument prepared by adding a piezoelectric polylactic acid material; and the tooth whitening instrument is a toothbrush, a tooth socket, or a tooth support prepared by adding a piezoelectric polylactic acid material.

In the present disclosure, unless otherwise specified, all parts are parts by weight.

The present disclosure has the following beneficial effects:

(1) The modified polylactic acid material obtained in the present disclosure has a piezoelectric constant ($d_{33}$) of 5.2-35.3 pC/N, which can reach the same level as a traditional piezoelectric material. Therefore, the modified polylactic acid material has the ability to efficiently catalyze dye/pigment degradation, namely having great application advantages in the fields of dye/pigment degradation and tooth whitening. For example, after 0.2 g of a powder sample is added into 100 mL of an IC dye aqueous solution with a concentration of 5 mg/L and then subjected to ultrasonic vibration at a frequency of 20 kHz and a power of 50 W for 120 min, the degradation efficiency of the IC dye aqueous solution is 82-98%. After the powder sample is subjected to the IC dye degradation experiment for 10 times, the degradation efficiency of the IC dye aqueous solution is still maintained at 78-94%.

(2) The piezoelectric polylactic acid powdered material having the ability to efficiently catalyze dye/pigment degradation prepared by the method provided by the present disclosure includes the biobased and biodegradable PLLA and PDLA as main components, and recyclable biological materials are used as sources of raw materials without depending on petroleum resources. The powder is non-toxic, mild, good in biocompatibility, and degradable. The waste powder can be directly discharged into the ecological environment to participate in the natural cycle, which is friendly, green and harmless to the ecological environment and the human body.

(3) As piezoelectric properties of the polylactic acid material obtained in the present disclosure are achieved by polarization caused by rotation of a chiral center, electret treatment or stretching treatment is not required to be conducted before use to endow the material with the piezoelectric properties, so that the material can be recycled repeatedly.

DESCRIPTION OF THE EMBODIMENTS

Figure 1:
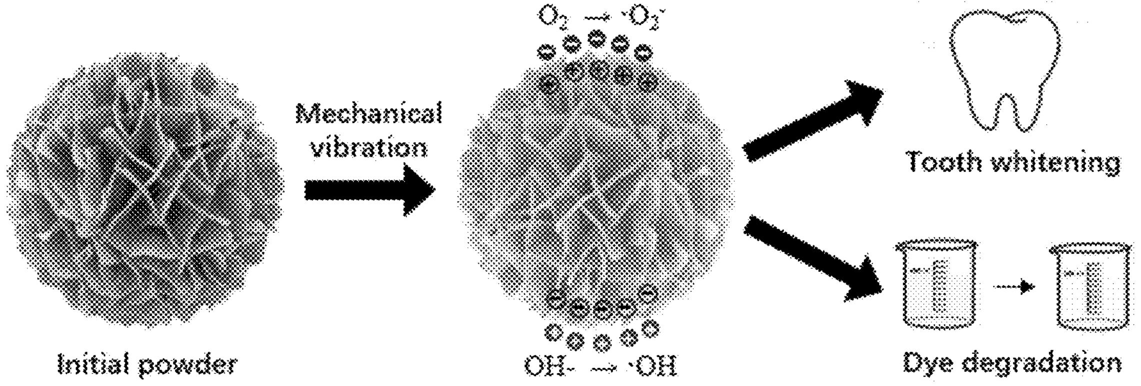
FIG. 1 is a schematic diagram showing a piezoelectric catalytic degradation mechanism of a piezoelectric polylactic acid powdered material having the ability to efficiently catalyze dye/pigment degradation provided by the present disclosure. From the schematic diagram, it can be seen that an SC-PLA powdered material with a layered stacking structure can achieve a piezoelectric effect under the action of mechanical vibration, and then generate reactive oxidation species (such as ·OH and $\cdot O_2^-$) having strong oxidation in water to catalyze dye/pigment degradation.

According to the present disclosure, a pore-forming agent having good compatibility with poly(L-lactic acid) and poly(D-lactic acid) is introduced. On the one hand, PLLA and PDLA molecular chains are endowed with good activity ability in a blending process, and the formation of a perfect lamellar crystal stacking structure is promoted while the crystallinity is improved, so that piezoelectric properties of a powdered material are improved. On the other hand, in a crystallization process, the pore-forming agent is removed from lamellar crystals to form a lamellar stacking phase separation structure, followed by etching with an optional solvent to form a lamellar stacking porous structure, so that the powder is endowed with more excellent piezoelectric properties.

Examples are provided below to describe the present disclosure in detail. However, it shall be noted that the following examples are merely used for further explaining the present disclosure, and cannot be understood as limitations of the protection scope of the present disclosure. Some non-essential improvements and adjustments made by a person skilled in the art according to the content of the present disclosure still fall within the protection scope of the present disclosure.

It is worth noting that (1) all parts of materials used in the following examples and comparative examples of the present disclosure are parts by weight; (2) scanning electron microscope photos of products obtained in the following examples and comparative examples and a $d_{33}$ coefficient of materials (the $d_{33}$ coefficient is one of coefficients commonly used for characterizing piezoelectric properties of a material, and a larger $d_{33}$ coefficient indicates stronger piezoelectric properties of a material) are measured by an American FE-SEM scanning electron microscope and a ZJ-3 piezoelectric tester, respectively; and (3) a pigment degradation experiment of the products obtained the following examples and comparative examples includes the following specific steps: 0.2 g of a sample is added into 100 mL of an indigo carmine (IC) dye aqueous solution with a concentration of 5 mg/L and then subjected to ultrasonic vibration at a frequency of 20 kHz and a power of 50 W for 30 min, and concentration changes of a pigment in the aqueous solution are measured by an ultraviolet spectrophotometer, where the ultraviolet spectrophotometer used is UV-3600 produced by Shimadzu of Japan.

Example 1

PLLA and PDLA having a weight-average molecular weight of $2.0*10^5$ g/mol and $1.5*10^5$ g/mol, respectively, were subjected to vacuum drying at a vacuum degree of less than 900 Pa at 60° C. until the water content was less than 200 ppm. 40 parts of a PEG (with an Mw of 10,000 g/mol) pore-forming agent, 0.3 part of a PEO-PLA-PEO compatibilizer, 30 parts of the PLLA and 30 parts of the PDLA were uniformly mixed by physical stirring. A resulting mixture was added into a torque rheometer, subjected to melting and blending at a temperature of 200° C. for 6 min, and then cooled to obtain an SC-PLA initial powder. The initial powder was placed in deionized water for selective etching of a PEG phase, and then dried to obtain a layered porous polylactic acid powder.

The powder has a $d_{33}$ coefficient of 35.3 pC/N. When the powder is used in an IC pigment degradation experiment, the degradation efficiency of the pigment is 98%. After the powder is used in the pigment degradation experiment for 10 times, the degradation efficiency of the pigment is 94%.

Example 2

PLLA and PDLA having a weight-average molecular weight of $1.0*10^4$ g/mol and $2.5*10^5$ g/mol, respectively, were subjected to vacuum drying at a vacuum degree of less than 900 Pa at 60° C. until the water content was less than 200 ppm. 30 parts of a PVAc pore-forming agent, 0.6 part of a PEO-PPO-PEO compatibilizer, 42 parts of the PLLA and 28 parts of the PDLA were uniformly mixed by physical stirring. A resulting mixture was added into a torque rheometer, subjected to melting and blending at a temperature of 190° C. for 3 min, and then cooled to obtain an SC-PLA initial powder. The initial powder was placed in cyclohexane for selective etching of a PVAc phase, and then dried to obtain a layered porous polylactic acid powder.

The powder has a $d_{33}$ coefficient of 22.8 pC/N. When the powder is used in an IC pigment degradation experiment, the degradation efficiency of the pigment is 93%. After the powder is used in the pigment degradation experiment for 10 times, the degradation efficiency of the pigment is 90%.

Example 3

PLLA and PDLA having a weight-average molecular weight of $1.0*10^5$ g/mol and $4.0*10^5$ g/mol, respectively, were subjected to vacuum drying at a vacuum degree of less than 900 Pa at 60° C. until the water content was less than 200 ppm. 10 parts of a PMMA pore-forming agent, 0.5 part of a PEO-PBA compatibilizer, 63 parts of the PLLA and 27 parts of the PDLA were uniformly mixed by physical stirring. A resulting mixture was added into a torque rheometer, subjected to melting and blending at a temperature of 180° C. for 5 min, and then cooled to obtain an SC-PLA initial powder. The initial powder was placed in acetone for selective etching of a PMMA phase, and then dried to obtain a layered porous polylactic acid powder.

The powder has a $d_{33}$ coefficient of 5.2 pC/N. When the powder is used in an IC pigment degradation experiment, the degradation efficiency of the pigment is 82%. After the powder is used in the pigment degradation experiment for 10 times, the degradation efficiency of the pigment is 78%.

Example 4

PLLA and PDLA having a weight-average molecular weight of $5.0*10^5$ g/mol and $3.0*10^5$ g/mol, respectively, were subjected to vacuum drying at a vacuum degree of less than 900 Pa at 60° C. until the water content was less than 200 ppm. 20 parts of a PHB pore-forming agent, 0.2 part of a PEO-PPO compatibilizer, 32 parts of the PLLA and 48 parts of the PDLA were uniformly mixed by physical stirring. A resulting mixture was added into a torque rheometer, subjected to melting and blending at a temperature of 210° C. for 4 min, and then cooled to obtain an SC-PLA initial powder. The initial powder was placed in dichloromethane for selective etching of a PHB phase, and then dried to obtain a layered porous polylactic acid powder.

The powder has a $d_{33}$ coefficient of 10.6 pC/N. When the powder is used in an IC pigment degradation experiment, the degradation efficiency of the pigment is 87%. After the powder is used in the pigment degradation experiment for 10 times, the degradation efficiency of the pigment is 83%.

Example 5

PLLA and PDLA having a weight-average molecular weight of $5.0*10^4$ g/mol and $1.0*10^5$ g/mol, respectively, were subjected to vacuum drying at a vacuum degree of less than 900 Pa at 60° C. until the water content was less than 200 ppm. 20 parts of a TBC pore-forming agent, 30 parts of the PLLA and 30 parts of the PDLA were uniformly mixed by physical stirring. A resulting mixture was added into a torque rheometer, subjected to melting and blending at a temperature of 170° C. for 8 min, and then cooled to obtain an SC-PLA initial powder. The initial powder was placed in ethanol for selective etching of a TBC phase, and then dried to obtain a layered porous polylactic acid powder.

The powder has a $d_{33}$ coefficient of 30.7 pC/N. When the powder is used in an IC pigment degradation experiment, the degradation efficiency of the pigment is 96%. After the powder is used in the pigment degradation experiment for 10 times, the degradation efficiency of the pigment is 92%.

Example 6

PLLA and PDLA having a weight-average molecular weight of $3.0*10^5$ g/mol and $1.0*10^4$ g/mol, respectively, were subjected to vacuum drying at a vacuum degree of less than 900 Pa at 60° C. until the water content was less than 200 ppm. 30 parts of a DOP pore-forming agent, 21 parts of the PLLA and 49 parts of the PDLA were uniformly mixed by physical stirring. A resulting mixture was added into a torque rheometer, subjected to melting and blending at a temperature of 180° C. for 9 min, and then cooled to obtain an SC-PLA initial powder. The initial powder was placed in ethanol for selective etching of a DOP phase, and then dried to obtain a layered porous polylactic acid powder.

The powder has a $d_{33}$ coefficient of 17.2 pC/N. When the powder is used in an IC pigment degradation experiment, the degradation efficiency of the pigment is 91%. After the powder is used in the pigment degradation experiment for 10 times, the degradation efficiency of the pigment is 88%.

Example 7

PLLA and PDLA having a weight-average molecular weight of $4.0*10^5$ g/mol and $2.0*10^5$ g/mol, respectively, were subjected to vacuum drying at a vacuum degree of less than 900 Pa at 60° C. until the water content was less than 200 ppm. 50 parts of a PEG (with an Mw of 10,000 g/mol) pore-forming agent, 0.1 part of a PEO-PPO compatibilizer, 25 parts of the PLLA and 25 parts of the PDLA were uniformly mixed by physical stirring. A resulting mixture was added into a torque rheometer, subjected to melting and blending at a temperature of 190° C. for 10 min, and then cooled to obtain an SC-PLA initial powder. The initial powder was placed in deionized water for selective etching of a PEG phase, and then dried to obtain a layered porous polylactic acid powder.

The powder has a $d_{33}$ coefficient of 28.9 pC/N. When the powder is used in an IC pigment degradation experiment, the degradation efficiency of the pigment is 95%. After the powder is used in the pigment degradation experiment for 10 times, the degradation efficiency of the pigment is 91%.

Example 8

PLLA and PDLA having a weight-average molecular weight of $2.5*10^5$ g/mol and $5.0*10^4$ g/mol, respectively, were subjected to vacuum drying at a vacuum degree of less than 900 Pa at 60° C. until the water content was less than 200 ppm. 20 parts of a PVAc pore-forming agent, 0.4 part of a PEO-PBA compatibilizer, 40 parts of the PLLA and 40 parts of the PDLA were uniformly mixed by physical stirring. A resulting mixture was added into a torque rheometer, subjected to melting and blending at a temperature of 220° C. for 7 min, and then cooled to obtain an SC-PLA initial powder. The initial powder was placed in cyclohexane for selective etching of a PVAc phase, and then dried to obtain a layered porous polylactic acid powder.

The powder has a $d_{33}$ coefficient of 13.8 pC/N. When the powder is used in an IC pigment degradation experiment, the degradation efficiency of the pigment is 89%. After the powder is used in the pigment degradation experiment for 10 times, the degradation efficiency of the pigment is 84%.

Comparative Example 1

PLLA and PDLA having a weight-average molecular weight of $2.0*10^5$ g/mol and $1.5*10^5$ g/mol, respectively, were subjected to vacuum drying at a vacuum degree of less than 900 Pa at 60° C. until the water content was less than 200 ppm. 40 parts of a PEO (with an Mw of 30,000 g/mol) pore-forming agent, 0.3 part of a PEO-PLA-PEO compatibilizer, 30 parts of the PLLA and 30 parts of the PDLA were uniformly mixed by physical stirring. A resulting mixture was added into a torque rheometer, subjected to melting and blending at a temperature of 200° C. for 6 min, and then cooled to obtain an SC-PLA initial powder. The initial powder was placed in deionized water for selective etching of a PEO phase, and then dried to obtain a layered porous polylactic acid powder.

The powder has a $d_{33}$ coefficient of 0.3 pC/N. When the powder is used in an IC pigment degradation experiment, the degradation efficiency of the pigment is 5%. After the powder is used in the pigment degradation experiment for 10 times, the degradation efficiency of the pigment is 1%.

Comparative Example 2

PLLA and PDLA having a weight-average molecular weight of $2.0*10^5$ g/mol and $1.5*10^5$ g/mol, respectively, were subjected to vacuum drying at a vacuum degree of less than 900 Pa at 60° C. until the water content was less than 200 ppm. 40 parts of a PEG (with an Mw of 10,000 g/mol) pore-forming agent, 0.3 part of a PEO-PLA-PEO compatibilizer, 30 parts of the PLLA and 30 parts of the PDLA were uniformly mixed by physical stirring. A resulting mixture was added into a torque rheometer, subjected to melting and blending at a temperature of 230° C. for 6 min, and then cooled to obtain an SC-PLA initial powder. The initial powder was placed in deionized water for selective etching of a PEG phase, and then dried to obtain a layered porous polylactic acid powder. When the powder is used in an IC pigment degradation experiment, the degradation efficiency of the pigment is 98%. After the powder is used in the pigment degradation experiment for 10 times, the degradation efficiency of the pigment is 94%.

The powder has a $d_{33}$ coefficient of 0.8 pC/N. When the powder is used in an IC pigment degradation experiment, the degradation efficiency of the pigment is 8%. After the powder is used in the pigment degradation experiment for 10 times, the degradation efficiency of the pigment is 2%.

Figures 2A, 2B, 2C:
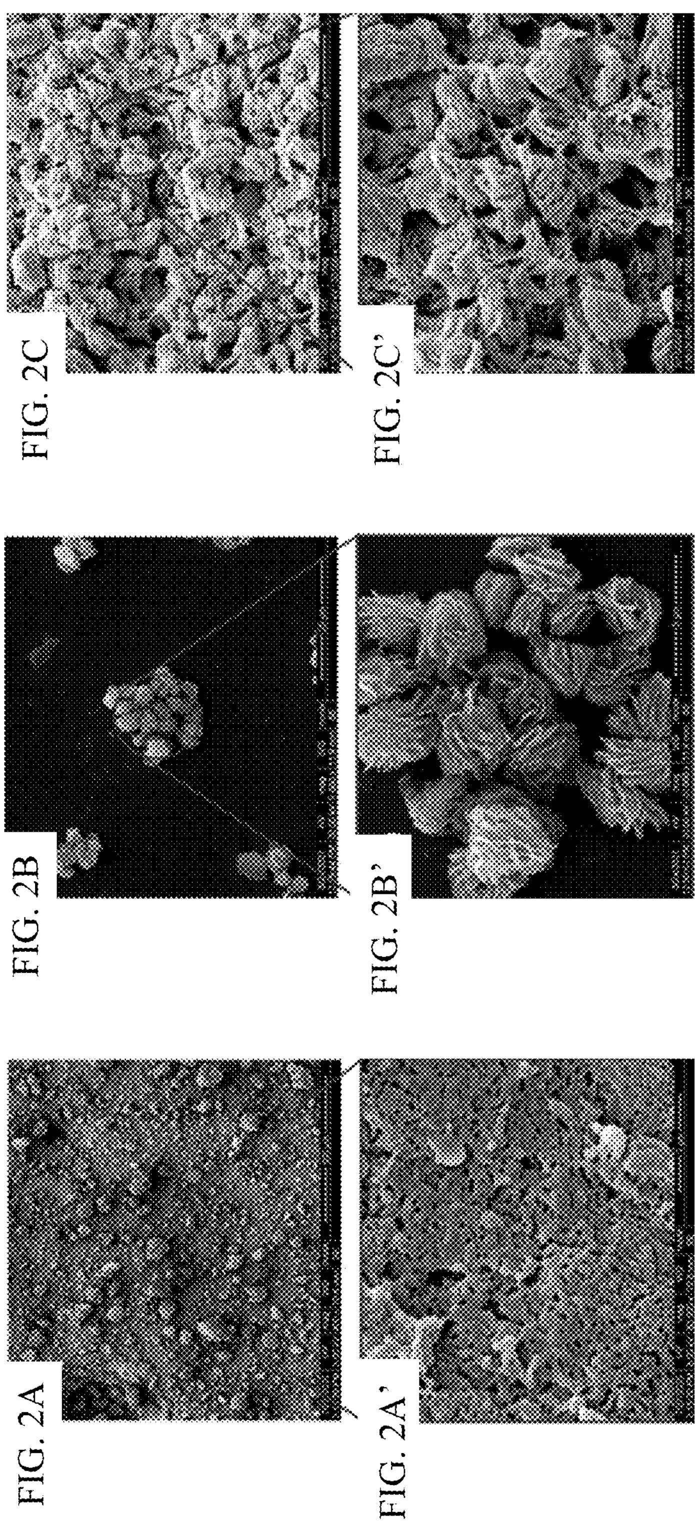
FIG. 2 shows scanning electron microscope (SEM) images of SC-PLA powdered materials prepared in Comparative Example 1 (FIG. 2A and FIG. 2A'), Example 1 (FIG. 2B and FIG. 2B') and Comparative Example 2 (FIG. 2C and FIG. 2C') of the present disclosure.
Figure 3:
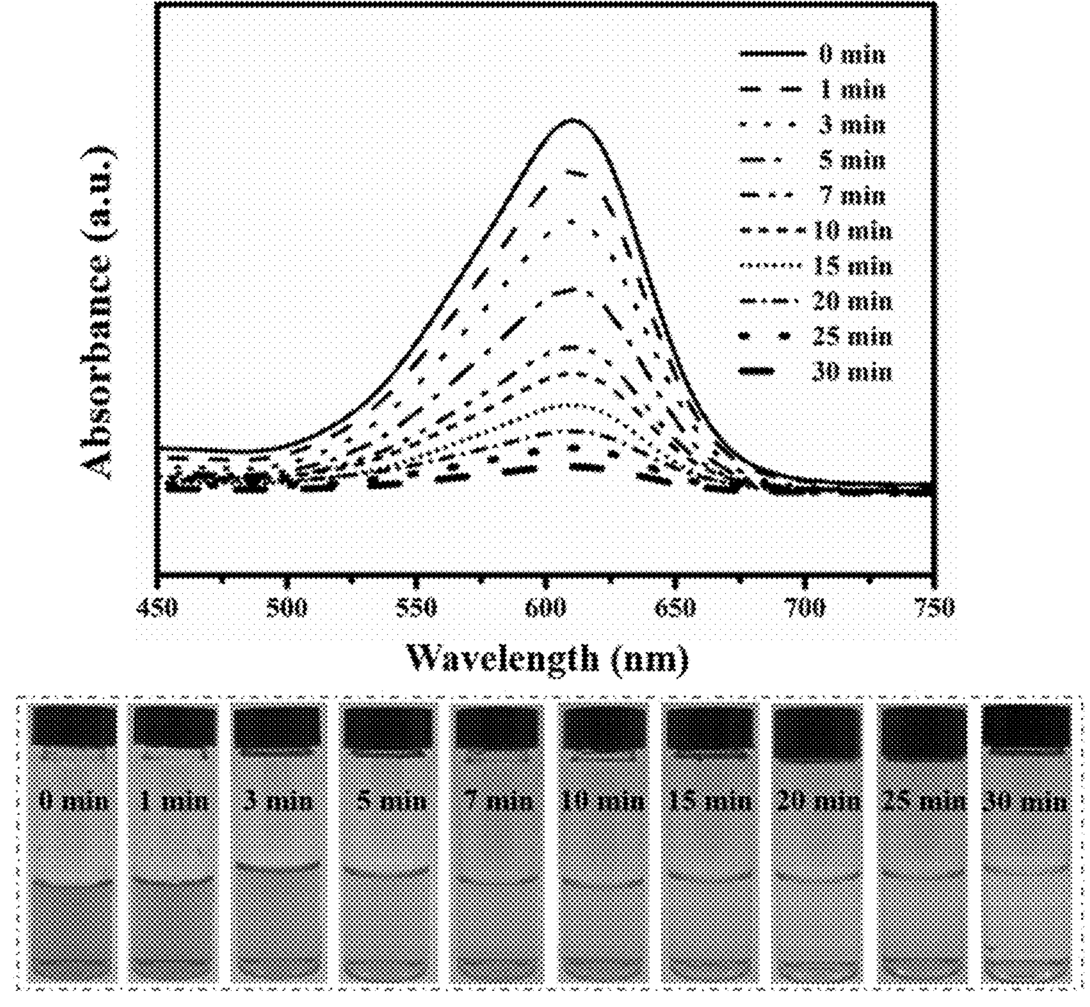
FIG. 3 shows a diagram (ultraviolet spectrum in an upper figure of FIG. 3) showing concentration changes of a pigment at different ultrasonic times when an SC-PLA powdered material prepared in Example 1 is used in an IC pigment degradation experiment and corresponding physical images (in a lower figure of FIG. 3). From the figure, it can be seen that with the increase of the ultrasonic time, an ultraviolet characteristic peak (at a wavelength of about 600 nm) of an IC pigment gradually becomes weak. When the ultrasonic time reaches 30 min, the pigment is basically completely degraded (the degradation efficiency is up to 98%), and an aqueous solution becomes colorless and transparent.
Figure 4:
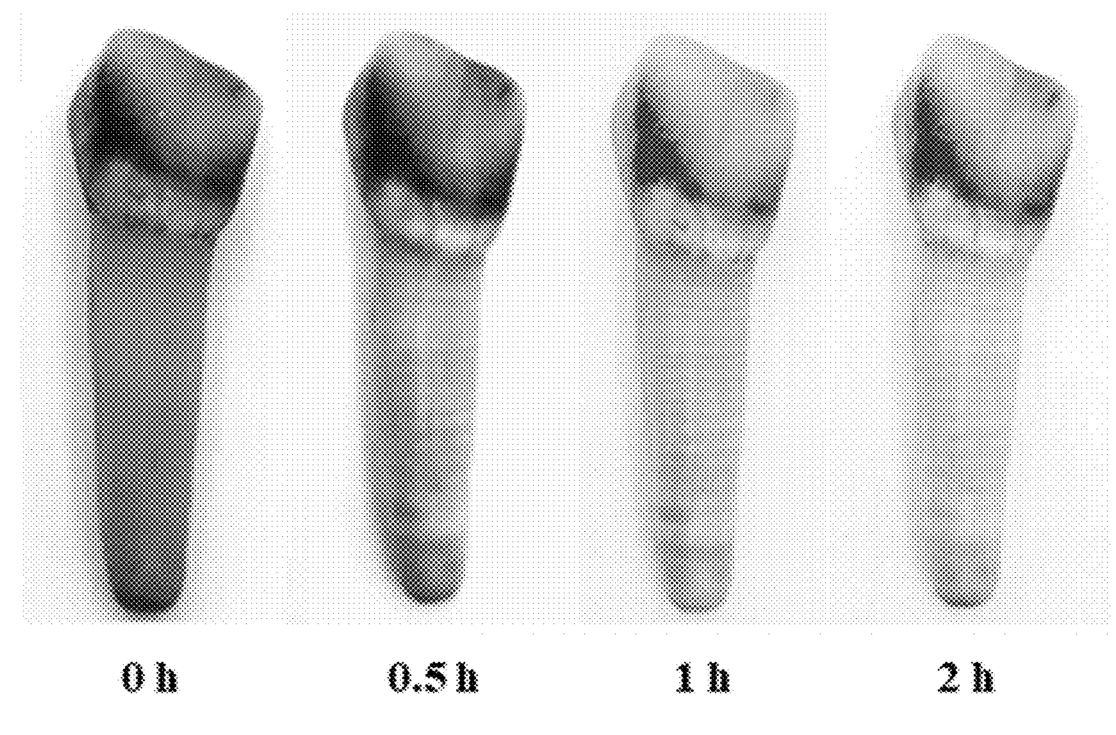
FIG. 4 shows the whitening ability of the SC-PLA powdered material prepared in Example 1 of the present disclosure for a stained bovine tooth. Specific steps are as follows: 0.5 g of the SC-PLA powder was evenly smeared on the surface of the wet tooth (the tooth was stained with a mixed liquid of coffee, tea and cola for a week), an electric toothbrush (with a vibration frequency of 30,000 Hz) was used for a brushing experiment, and photos were taken every 30 min for recording.

Performance Test:

In the present disclosure, the microstructure of the composite materials obtained in Example 1 and Comparative Examples 1-2 is tested, and results are as shown in FIG. 2. From FIG. 2A and FIG. 2A', it can be seen that in Comparative Example 1, the PEO (with an Mw of 30,000 g/mol) pore-forming agent used has poor compatibility with the PLA matrix, phase separation from the PLA matrix is conducted in a melt state to obtain an island-like porous structure, and the powder has large powder particles and uneven size, so that the structure has little effect of improving the piezoelectric properties, and the $d_{33}$ coefficient is only 0.3 pC/N. In Example 1 (FIG. 2B and FIG. 2B'), the PEG (with an Mw of 10,000 g/mol) pore-forming agent used has good compatibility with the PLA matrix (the blend has a homogeneous structure in a molten state), and phase separation is conducted after the PLA matrix is crystallized to form a layered stacking structure, so that the finally obtained powder has excellent piezoelectric properties, and the $d_{33}$ coefficient is as high as 35.5 pC/N. In Comparative Example 2, the PEG (with an Mw of 10,000 g/mol similar to that in Example 1) pore-forming agent used has good compatibility with the PLA matrix, but the processing temperature is as high as 230° C. (very close to the melting point of SC-PLA), and the layered porous structure of the powder is almost destroyed, so that the piezoelectric properties are greatly reduced, and the $d_{33}$ coefficient is only 0.8 pC/N.

The invention claimed is:

1. A piezoelectric polylactic acid material, having a porous structure comprising stacked layers, wherein the piezoelectric polylactic acid material is prepared by a method comprising the steps of:

subjecting a mixture comprising poly(L-lactic acid), poly (D-lactic acid), and a pore-forming agent to melting and blending at 170-220° C. to obtain a blend; and removing the pore-forming agent from the blend to obtain the piezoelectric polylactic acid material, the pore-forming agent being compatible with the polylactic acid, wherein the mixture further comprises 0.1-0.6 part by weight of a compatibilizer, and the compatibilizer is an amphiphilic compound.

2. The piezoelectric polylactic acid material according to claim 1, wherein the piezoelectric polylactic acid material has a piezoelectric constant of 5.2-35.3 pC/N.

3. The piezoelectric polylactic acid material according to claim 1, wherein the pore-forming agent is selected from polyethylene glycol, polyvinyl acetate, polymethyl methacrylate, polyhydroxybutyric acid, tributyl citrate, and dioctyl phthalate.

4. The piezoelectric polylactic acid material according to claim 1, wherein the mixture comprises 30-70 parts by weight of the poly(L-lactic acid), 30-70 parts by weight of the poly(D-lactic acid), 10-50 parts by weight of the pore-forming agent, and 0.1-0.6 part by weight of the compatibilizer.

5. The piezoelectric polylactic acid material according to claim 1, wherein the pore-forming agent is removed from the blend by placing the blend in a solvent to dissolve the pore-forming agent without dissolving the polylactic acid, and the solvent is selected from water, ethanol, acetone, cyclohexane, n-hexane, dichloromethane, and trichloromethane.

6. A piezoelectric polylactic acid material according to claim 1, configured for use in tooth whitening, dye/pigment degradation, piezoelectric sensing, ultrasonic imaging, in vivo drivers, or implantable piezoelectric devices for induced regeneration of tissues.

7. A tooth whitening material, wherein the tooth whitening material is a piezoelectric polylactic acid material according to claim 1.

8. A tooth whitening product, wherein the tooth whitening product is a tooth whitening agent or a tooth whitening instrument comprising the piezoelectric polylactic acid material according to claim 1.

9. The piezoelectric polylactic acid material according to claim 4, the compatibilizer is selected from a polyethylene oxide-propylene oxide-ethylene oxide block copolymer, a polyethylene oxide-propylene oxide block copolymer, a polyethylene oxide-lactic acid-ethylene oxide block copolymer, and a polyethylene oxide-butyl acrylate block copolymer.

10. The piezoelectric polylactic acid material according to claim 1, wherein the poly(L-lactic acid) has a weight-average molecular weight of $1*10^4$-$5*10^6$ g/mol and an optical purity of equal to or greater than 90%, and the poly(D-lactic acid) has a weight-average molecular weight of $1*10^4$-$5*10^6$ g/mol and an optical purity of equal to or greater than 90%.

11. The tooth whitening product according to claim 8 is in a form of a powder, a liquid, a gum, a gel, a paste, or a fiber.

12. The tooth whitening product according to claim 8 is a toothpaste, a tooth powder, a gum, a chew gum, a gel, a tooth cleaning solution, a tooth scrub, a mouthwash, or a medical floss containing piezoelectric polylactic acid.

13. The tooth whiten product according to claim 8 is a toothbrush, a tooth socket, or a tooth support.

* * * * *